US00PP17377P2

(12) United States Plant Patent
Olesen

(10) Patent No.: US PP17,377 P2
(45) Date of Patent: Jan. 23, 2007

(54) MINIATURE ROSE PLANT NAMED 'POULPAH037'

(50) Latin Name: ***Rosa* hybrid**
Varietal Denomination: Poulpah037

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 17 days.

(21) Appl. No.: 11/266,617

(22) Filed: Nov. 4, 2005

(51) Int. Cl.
*A01H 5/00* (2006.01)

(52) U.S. Cl. ..... Plt./121

(58) Field of Classification Search ..... Plt./122, Plt./121, 129

See application file for complete search history.

*Primary Examiner*—Kent Bell
*Assistant Examiner*—June Hwu

(57) ABSTRACT

A new miniature rose plant named 'Poulpah037' that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah037'.

SUMMARY OF THE INVENTION

The present invention constitutes a new and distinct variety of miniature rose plant which originated from a controlled crossing between the female seed parent, an unnamed seedling, and the male pollen parent an-unnamed seedling.

The two parents were crossed during the summer of 2002 and the resulting seeds were planted in a controlled environment in Fredensborg, Denmark. The new variety, named 'Poulpah037', originated as a single seedling from the stated cross.

The new variety may be distinguished from its female seed parent mainly in that 'Poulpah037' is more compact in growth habit than the seed parent.

The new variety may be distinguished from its male pollen parent by the following combination of characteristics:

1. Flowers of the pollen parent have more than 50 flower petals, while flowers of 'Poulpah037' have 15 to 20 flower petals.
2. Flowers of 'Poulpah037' are deep pink to red while the pollen parent has flowers which are medium pink.

The objective of the hybridization of this rose variety for commercial culture was to create a new and distinct variety with unique qualities, such as:

1. Uniform and abundant red flowers that retain their color as flowers mature;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpah037' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah037' was selected by the inventor as a single plant from the progeny of the hybridization in April 2003.

Asexual reproduction of 'Poulpah037' by cuttings and traditional budding was first done by Mogens N. Olesen in the nursery in Fredensborg, Denmark in 2003. This initial and other subsequent propagations conducted in controlled environments have demonstrated that the characteristics of 'Poulpah037' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah037'. Specifically illustrated in the drawing:

FIG. 1.1; Flower bud closed, and partially open;

FIG. 1.2; Cluster of flower buds and partially open flower attached to stem;

FIG. 1.3; Open flowers;

FIG. 1.4; Flower petals, detached;

FIG. 1.5; Sepals, pedicel, and receptacle, revealing reproductive parts;

FIG. 1.6; Juvenile leaves;

FIG. 1.7; Bare stem;

FIG. 1.8; Mature leaves.

DETAILED DESCRIPTION OF THE VARIETY

The following is a description of 'Poulpah037', as observed in its growth in glasshouses in Fredensborg, Denmark. Observed plants are 4 months of age and were cultivated in 12 cm pots. Color references are made using The Royal Horticultural Society (London, England) Colour Chart, 2001, except where common terms of color are used.

For a comparison, several physical characteristics of the rose variety 'Poulac016', described and illustrated in U.S. Plant Pat. No. 15,874, are compared to 'Poulpah037' in Chart 1.

CHART 1

| | 'Poulpah037' | 'Poulac016' |
|---|---|---|
| Petal Count: | 15 to 20 petals | 100 petals |
| Flower Diameter: | 60 to 90 mm | 46 mm |
| General Tonality of Flower Color: | Red-Purple Group N57A to Red Group 53C | Red-Purple 57A |

FLOWER AND FLOWER BUD

Blooming habit: Continuous.

Flower bud:

*Size.*—Upon opening, 25 mm in length from base of receptacle to end of bud. 12 mm in diameter.

*Bud form.*—Pointed ovate.

*Bud color.*—As sepals unfold, petals are Red Group 53A to 53B.

*Sepals.*—Upper Surface: Color: Green Group 138B. Anthocyanic pigments observed on the apex colored Greyed-Red Group 178A. Surface: Weak pubescence. Lower Surface: Color: Yellow-Green Group 146A. Texture: Somewhat rough with stipitate glands and light pubescence. Shape: Apex: Cirrhose. Base: Flat at union with receptacle. Margins: Margins have medium to weak foliaceous appendages on three of the five sepals. Stipitate glands are abundant. Size: 23 to 26 mm long by 7 to 9 mm wide.

*Receptacle.*—Surface Texture: Smooth. Shape: Urn-shaped. Size: 7 mm (h)×10 mm (w). Color: Yellow-Green Group 144A. Anthocyanin: None observed.

*Pedicel.*—Surface: Rough with stipitate glands. Length: 25 mm average length. Diameter: 4 mm. Color: Yellow-Green Group 144A. Strength: Strong. Scent: Stipitate glands release sweet scent when touched.

*Borne.*—Both singularly and in clusters of 3 flower buds per stem. Inflorescence type is a panicle.

Flower bloom:

*Fragrance.*—None.

*Duration.*—As a pot plant, flowers last more than 28 days. After flowers have fully matured, petals adhere to the receptacle.

*Size.*—Fully open diameter is 60 to 90 mm. Depth is 35 mm.

*Form.*—Flowers resemble a typical hybrid tea rose shape with petals tightly closed for the first few days of development. Afterwards petals unfold, reflex, and overlap with a somewhat undulated form, expanding the blossom to its full diameter.

*Shape of flower, side view.*—Upon opening, the upper portion is flat. The lower portion is flat. After opening, the upper portion is flat convex. The lower portion is concave.

Petalage: 15 to 20 petals under normal conditions, 5 of which are petaloids.

Flower color:

*Upon opening, petals.*—Outermost and innermost petals: Upper Surface: Red-Purple Group N57A to Red Group 46A with occasional streaks of Red-Purple Group 69C. Lower Surface: Red-Purple Group 58A to Red-Purple Group N57A with intonations of Red-Purple Group 59B towards the basal zone. Occasional streaks of Red-Purple 69C appear.

*Upon opening, basal petal spots.*—Upper Surface: Yellow Group 4D. Lower Surface: Yellow Group 4D.

*After opening, petals.*—Outermost and innermost petals: Upper Surface: Red-Purple Group N57A with occasional petal streaking the color of Red-Purple 69C. Lower Surface: Red-Purple Group N57A to N57B with occasional streaking of White Red-Purple Group 69C.

*After opening, basal petal spots.*—Upper Surface: Yellow Group 4D. Lower Surface: Yellow Group 4D.

General tonality: On newly opened flowers the flower color is Red-Purple Group N57A to Red Group 53C. Mature flower color becomes Red-Purple Group N57A to N57C.

Petals:

*Petal reflex.*—Slightly reflexed.

*Petal margin.*—Entire and uniform. Slightly undulated.

*Shape.*—Broad elliptical. Base: Acute and obtuse. Apex: Rounded.

*Size.*—42 to 48 mm in length. 50 to 55 mm wide.

*Thickness.*—Above average.

*Texture.*—Smooth.

Petaloids:

*Size.*—Generally 35 mm long; 35 mm wide.

*Shape.*—Apex may be rounded, however often there is a cleft dividing the petaloid. Base shape is acute.

*Color.*—Upper Surface: Red-Purple Group N57A with occasional streaking of Red-Purple 69C. Lower Surface: Red-Purple Group N57A with occasional streaking of Red-Purple Group 69C and White Group N155B.

Reproductive organs:

*Pollen.*—None observed.

*Anthers.*—Size: 4 mm long. Color: Yellow Group 4D. Quantity: 55 to 65.

*Filaments.*—Color: Red Group 48A. Length: Approximately 8 to 9 mm.

*Pistils.*—Length: Approximately 6 mm long. Quantity: 35 to 40.

*Stigmas.*—Inferior in location relative to the length of the filaments and the height of the anthers. Color: Yellow-White Group 158A.

*Styles.*—Color: Red Group 43A.

*Seed formation.*—Not observed.

PLANT

Plant growth: Moderate upright and bushy. When grown as a 12 cm pot plant on its own roots, the average height of the plant itself is 22 to 25 cm and the average width is 20 cm.

Stems:

*Color.*—Young wood: Yellow-Green Group 146B. Older wood: Yellow-Green Group 146B.

*Internodal distance.*—23 mm.

*Length of stems.*—13 to 15 cm from the base of the stem to the flowering portion.

*Diameter.*—3 to 4 mm.

*Surface texture.*—Young wood: Smooth. Older wood: Smooth.

Prickles:

*Incidence.*—5 to 6 prickles per 10 cm of stem.

*Size.*—Normally 5 to 6 mm.

*Color.*—Juvenile prickles are Greyed-Red Group 181D. Mature prickles are Greyed-Red Group 181D.

*Shape.*—Upper side: Convex. Lower side: Concave.

Plant foliage: Normal number of leaflets on normal leaves in middle of the stem: 5 to 7 leaflets.

*Compound leaf size.*—85 mm (l)×65 mm (w).

*Quantity.*—4 leaves per 10 cm of stem.

*Color.*—Juvenile foliage: Upper Leaf Surface: Yellow-Green Group 146B. Margins have anthocyanic pigments the color of Greyed-Purple Group 183B. Lower Leaf Surface: Yellow-Green Group 146C. Mature foliage: Upper Leaf Surface: Yellow-Green Group 147A. Lower Leaf Surface: Yellow-Green Group 147B.

Plant leaves and leaflets:

*Stipules.*—Size: 6 mm in length. Shape: Linear, slightly broad based with outward extending apecies. Margins: Finely serrated with few stipitate glands. Color: Yellow-Green Group 146A.

*Petiole.*—Length: Normally 12 mm in length. Diameter: 1.5 mm on average. Upper Surface: Color: Yellow-Green Group 144A. Anthocyanin: Greyed-Orange Group 166A. Underneath: Few stipitate glands observed. Lower Surface: Color: Yellow-Green Group 144B. Underneath: Few small prickles observed.

*Rachis.*—Size: Normally 25 mm in length. Upper Surface: Color: Yellow-Green Group 144A. Anthocyanin: Greyed-Orange Group 166A. Observations: Few stipitate glands. Lower Surface: Color: Yellow-Green Group 144B. Observations: Few small prickles.

*Leaflet.*—Size: 40 to 45 mm in length by 30 to 33 mm wide. General Shape: Ovate. Apex Shape: Acute. Base Shape: Rounded. Texture: Smooth. Thickness: Average. Arrangement: Odd pinnate. Venation: Reticulate. Leaf Gloss: Glossy finish.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulpah037', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

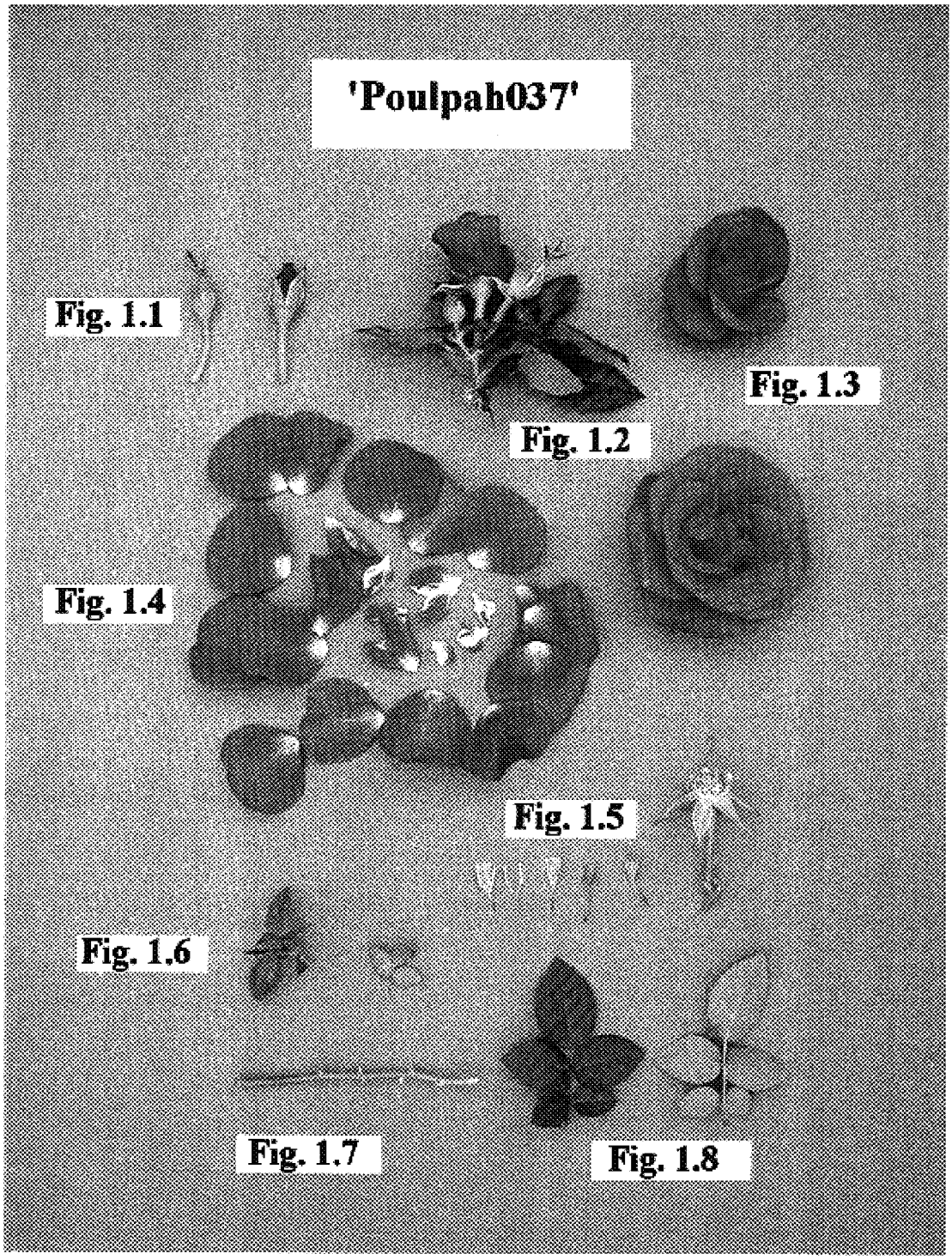
'Poulpah037'
Fig. 1.1
Fig. 1.2
Fig. 1.3
Fig. 1.4
Fig. 1.5
Fig. 1.6
Fig. 1.7
Fig. 1.8